United States Patent [19]
Evans et al.

[11] 3,971,950
[45] July 27, 1976

[54] INDEPENDENT COMPRESSION AND POSITIONING DEVICE FOR USE IN MAMMOGRAPHY

[75] Inventors: David T. Evans, Manhattan Beach; Ellen M. Proctor, Pasadena; Frank R. Brion, Arcadia; Theodorus M. Ceelen, La Verne, all of Calif.

[73] Assignee: Xerox Corporation, Stamford, Conn.

[22] Filed: Apr. 14, 1975

[21] Appl. No.: 567,797

[52] U.S. Cl. ............................ 250/451; 269/328; 250/456
[51] Int. Cl.² ................. G21K 5/08; G01N 21/00; G01N 23/00; A61G 13/00
[58] Field of Search ................ 250/456, 451, 439; 269/328

[56] References Cited
UNITED STATES PATENTS

| | | | |
|---|---|---|---|
| 3,381,684 | 5/1968 | Anderson | 269/328 |
| 3,578,971 | 5/1971 | Lasky | 250/456 |
| 3,810,462 | 5/1974 | Szpur | 269/328 |

*Primary Examiner*—Alfred E. Smith
*Assistant Examiner*—T. N. Grigsby
*Attorney, Agent, or Firm*—J. E. Beck; T. J. Anderson; A. W. Karambelas

[57] ABSTRACT

A mammographic compression and positioning device which is independent of the x-ray system utilized to produce images of an object being examined. A slide assembly is movable along a vertical post member which is adjustably secured to a base member. A compression paddle is coupled to the slide assembly and has a curved lower surface which, upon contacting the object, exerts a variable compressive force thereon. The position of the compression paddle is adjustable in a plurality of directions, allowing the paddle to be exactly positioned whereby an image of a selected object view may be obtained. The compression paddle is transparent enabling the user of the device to visualize the object being compressed and to take the steps necessary to provide initial image results which are satisfactory thereby reducing the number of reimages which normally would be required.

15 Claims, 5 Drawing Figures

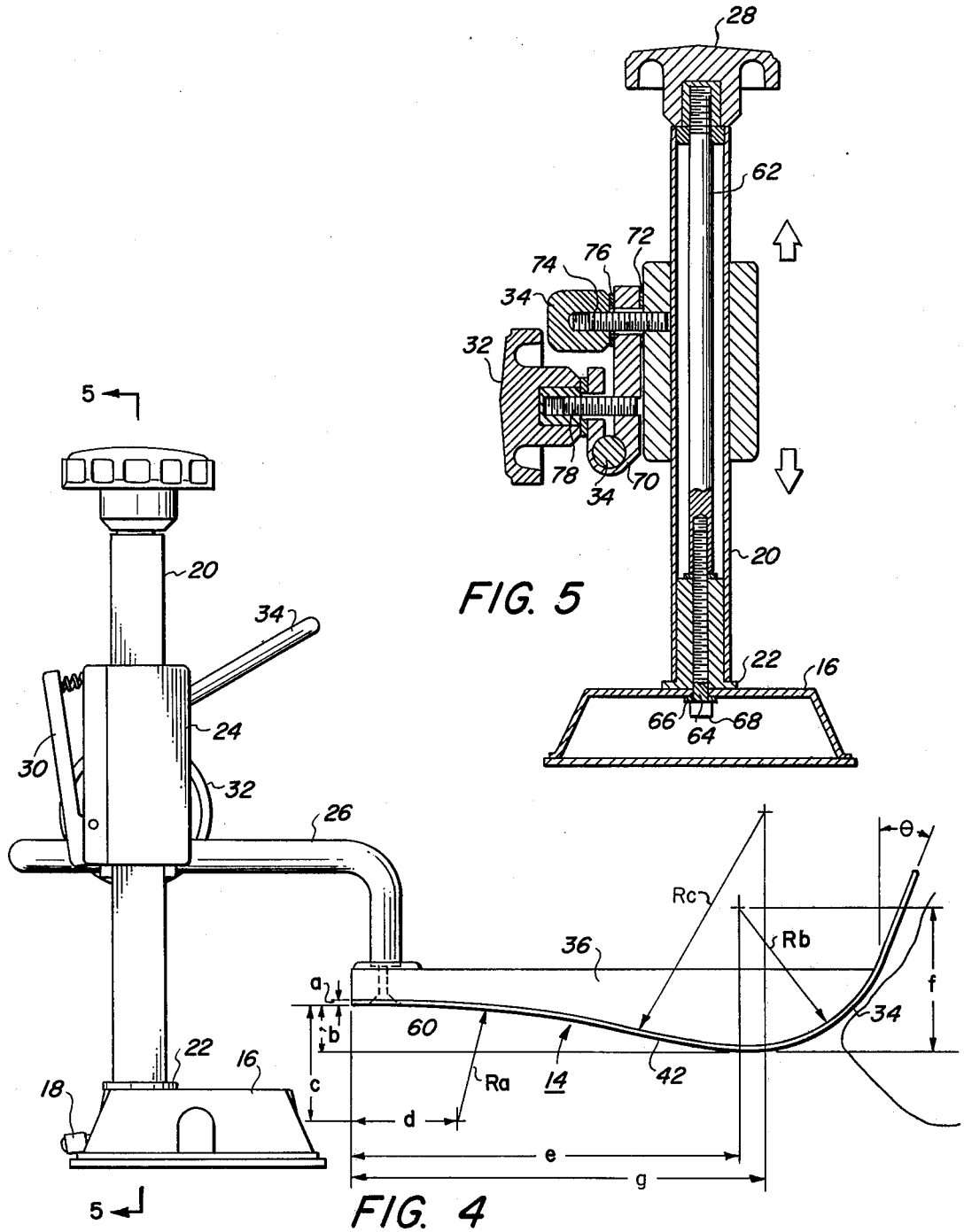

INDEPENDENT COMPRESSION AND POSITIONING DEVICE FOR USE IN MAMMOGRAPHY

BACKGROUND OF THE INVENTION

Breast compression in the mammographic field is necessary to provide images of improved quality since the breast is an object of wide geometric change. For example, compression has reduced the thickness variation of the breast from the nipple to the chest wall. An image of the compressed breast therefore will provide more uniform information in the developed image. Breast compression also inhibits the movement of the breast during exposure thereby reducing image degradation due to breast movement.

Prior art x-ray systems, such as that shown in U.S. Pat. No. 3,824,397, generally incorporate integral compression devices. The degree of flexibility in positioning the integral device to accommodate the desired image view or breast size is limited by the associated x-ray system. Further, the non-universality of integral compression devices limit their capability of incorporating significant improvements in breast compression devices and techniques. An independent compression device will serve those users having an existing x-ray facility who are unwilling to dedicate a portion of the equipment to mammography.

The breast compression device, in addition to being independent of the x-ray system, should preferably be lightweight and portable and incorporate a compression member which may be adjusted in a plurality of directions, allows breast visualization during compression and provides for optimum compression over the contacted breast area.

SUMMARY OF THE PRESENT INVENTION

The present invention provides a mammographic compression and positioning device which is independent of x-ray system utilized to produce images of an object being examined. A slide assembly is movable along a vertical post member which is adjustably secured to a base member. A compression paddle is coupled to the slide assembly and has a curved lower surface which, upon contacting the object, exerts a variable compressive force thereon. The position of the compression paddle is adjustable in a plurality of directions, allowing the paddle to be exactly positioned whereby an image of a selected object view may be obtained. The compression paddle is transparent enabling the user of the device to visualize the object being compressed and to take the steps necessary to provide initial image results which are satisfactory thereby reducing the number of reimages which normally would be required.

It is an object of the present invention to provide a compression device for use in mammography which is independent of the x-ray system and imaging member.

It is a further object of the present invention to provide a breast compression device which is independent of the x-ray system and imaging member which is adjustable in a plurality of directions enabling the device to be positioned whereby an image of a selected breast view may be obtained.

It is still a further object of the present invention to provide a breast compression device which is independent of the x-ray system and imaging member and which includes a compression member having a curved lower portion which exerts optimum compression over the contacted area of the breast, by bringing the breast away from the chest wall and aiding in the separation of structure within the breast.

It is still an object of the present invention to provide a breast compression device which is independent of the x-ray system and imaging member and which includes a transparent compression member having a curved lower portion which exerts variable pressure over the contacted area of the breast and which allows a user to visually verify the position of the breast with respect to the imaging member and to verify the absence of skin folds prior to imaging.

It is a further object of the present invention to provide a breast compression device which is independent of the x-ray system and imaging member and is lightweight and portable.

DESCRIPTION OF THE DRAWINGS

For a better understanding of the invention, as well as other objects and features thereof, reference is made to the following description, which is to be read in conjunction with the accompanying drawings wherein:

FIG. 4 is a side view of the independent compression device; and

FIG. 5 is a rear sectional view of the independent compression device.

DESCRIPTION OF THE PREFERRED EMBODIMENT

Figure 1:
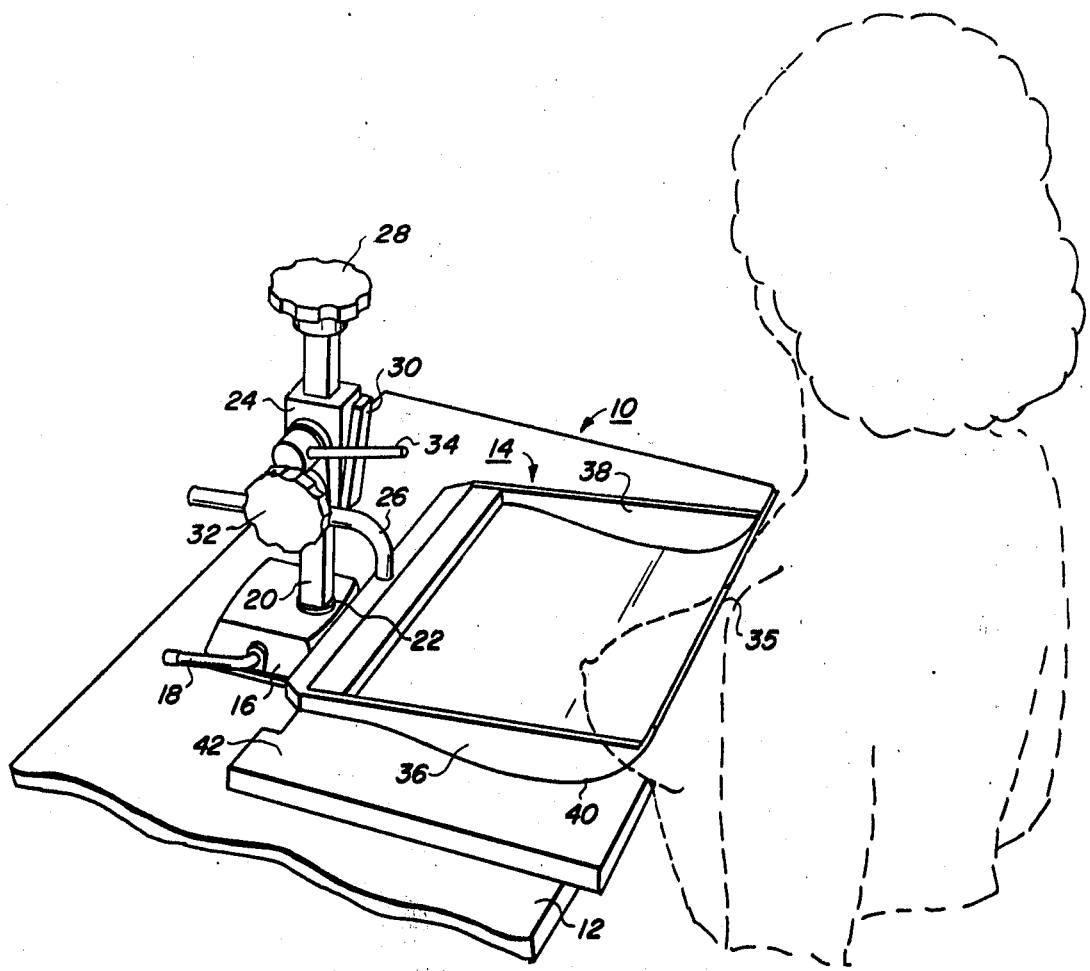
FIG. 1 is a perspective view of the independent compression device of the present invention illustrating the device positioned for a craniocaudad view of the breast.

FIG. 1 shows an x-ray cassette and subject in position for a craniocaudad view of the subject's breast, the breast being properly positioned and compressed by the independent compression device 10 of the present invention. The compression device 10 is attached to a flat surface 12 which may be independent of the x-ray system or on the x-ray table itself. Compression device 10, in essence, comprises a compression paddle 14 made of transparent, radio-translucent, material, such as "Lexan," a polycarbonate organic resin from General Electric Company, which allows the user, or technologist, to visually confirm the position of the breast prior to x-ray exposure, insure maximum compression and eliminate skin folds to provide images of improved quality while reducing the necessity for reimaging. A vacuum base 16 having a vacuum base lock and release lever 18 is secured to the supporting surface 12, square shaped post member 20 being rotatably supported in base 16 via a bushing 22. The compression paddle 14 is supported in slide assembly 24 via paddle support arm 26. Knob 28 is provided to allow the device (except the vacuum base 16) to rotate in a horizontal plane. Vertical pressure release member 30 allows control of the vertical position of the compression paddle 14 along post member 20. Knob 32 allows the paddle 14 to rotate around support arm 26 thereby providing adjustment of the paddle position for the exaggerated medial and lateral craniocaudad views and accommodating subjects with stomach protrusions and prominent rib cages in the lateral views and allowing an in and out motion for proper location of the paddle 14 directly against the chest wall.

Lever 32 provides a tilting type movement for the compression paddle which allows for maximum compression in the thick part of the breast. Compression paddle 14 comprises an upwardly curved lip portion 35 and side members 36 and 38. To allow the compression paddle 14 to apply maximum compression (pressure) in the area of the breast near the chest wall (retromammary area) with minimum compression in the nipple area (subareolar area), the lower surface 40 of the compression paddle 14 has a uniquely designed curved shape as shown.

Figure 2:
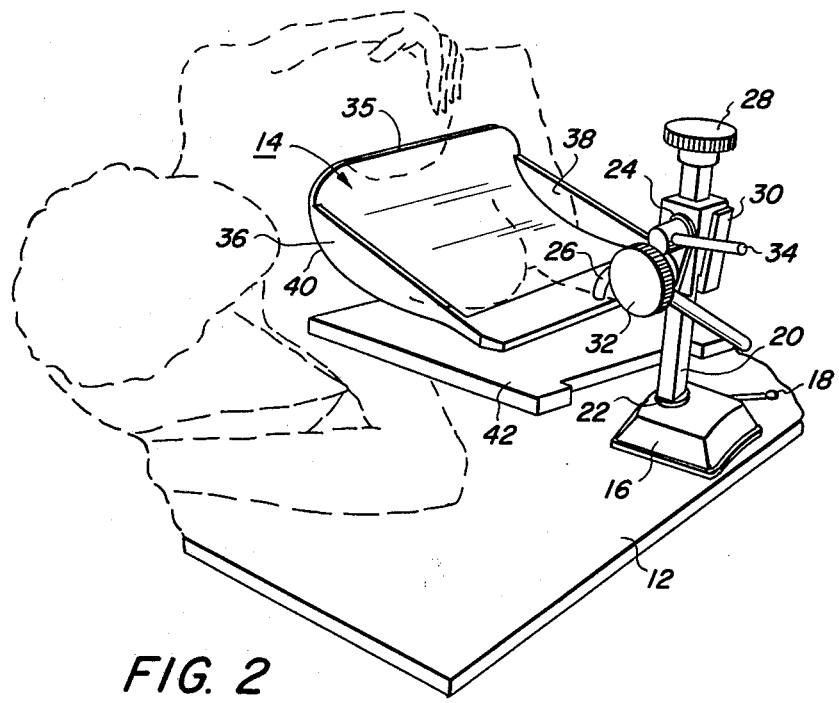
FIG. 2 is a perspective view of the independent compression device of the present invention illustrating the device positioned for a contact medio-lateral view.

Although the subject to be examined is shown positioned for the craniocaudad and contact medio-lateral views in FIGS. 1 and 2, respectively, the positioning flexibility of the independent compression device of the present invention due to the degrees of freedom associated with the positioning of the compression paddle 14 allows additional supplementary views to be imaged.

As shown in FIGS. 1 and 2, the breast of the subject is positioned between the lower surface 40 of the compression paddle 14 and an imaging member holder or cassette 42. The cassette 42 is of the type described in U.S. Pat. No. 3,827,072 which has a charged xerographic plate contained therein. Alternately, the cassette 42 may comprise a standard x-ray film in a paper pack or cassette. The independent compression device, it should be noted, may be utilized with xeroradiographic and film mammographic systems.

In operation, a xerographic plate is first charged and then inserted in the cassette 42, the cassette thereafter being positioned as shown in FIGS. 1 and 2. After the user or technologist adjusts independent compression device 10 to properly position and compress the breast, the x-ray source (not shown) is energized and an image of the breast is formed on the xerographic plate. The cassette is then removed and the image is developed. Apparatus for automatically charging the xerographic plate and developing the image formed therein is set forth in U.S. Pat. No. 3,640,246.

In the contact medio-lateral view shown in FIG. 2, the cassette 42 rests on the arm of the subject at an angle to surface 12 with compression plate 14 positioned as shown.

Figure 3:
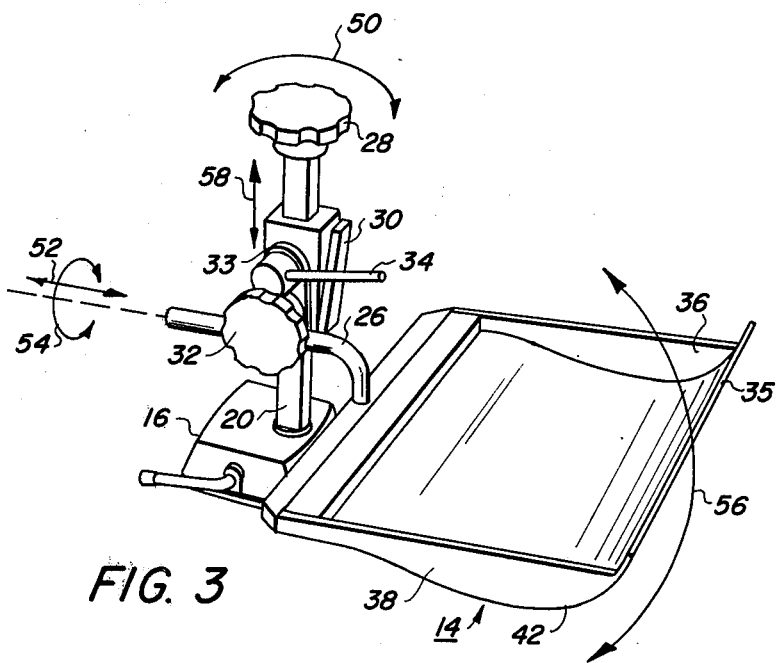
FIG. 3 is a perspective view of the independent compression device of the present invention illustrating the degrees of freedom of the compression paddle.

FIG. 3 is a perspective view of the independent compression device of the present invention and illustrates the adjustable positions of the compression paddle 14. The same reference numerals, it should be noted, are utilized to identify the identical elements in each figure.

By appropriate adjustment of knob 28, the entire independent compression device 10, except for vacuum base 16, is rotatable around the horizontal (in direction of arrow 50). This rotation allows for proper compression for exaggerated medial and lateral craniocaudad view and for different thicknesses of the breast in the lateral view.

Adjustment of lever 34 allows the compression paddle 14 (and support arm 26, paddle clamp 33, knob 32 and lever 34) to tilt in the direction of arrow 56 whereby maximum compression can be applied to the thick part of the breast.

By pressing vertical pressure release member 30, slide assembly 24 is movable in the direction of arrow 58 which allows for compression of the breast and adjustment for different breast sizes.

FIG. 4 is a side view of the independent compression device of the present invention and FIG. 5 is a sectional view of FIG. 4 along line 5—5. As set forth hereinabove, the square post member 20 is rotatably mounted to base 16 via bushing 22. The base member 16 and the vacuum base lock and release lever 17 operate to provide a suction connection to a flat surface. A flat head screw 60 joins the compression paddle 14 to support arm 26. The compression paddle 14 is made of a transparent, x-ray transmissive material, such as Lexan, and comprises two edge members 36 and 38 (FIGS. 1 and 2) and a lower surface of a predetermined curvature. As set forth hereinabove, the curved design for the compression paddle allows slightly greater pressure to be exerted on the chest wall than on the area closer to the nipple therefore providing an object of essentially constant thickness variation which provides higher quality images. The paddle curvature also allows the breast to be positioned away from the chest wall, aiding in the separation of structures within the breast and minimizes subject discomfort during the examination. Although the particular curvature and other paddle dimensions may be varied, the following are typical of those which may be utilized to provide the advantages set forth hereinabove:

$a = 0.035$ inches
$b = 0.750$ inches
$c = 2.72$ inches
$d = 1.60$ inches
$e = 6.76$ inches
$f = 2.64$ inches
$g = 6.77$ inches
$R_a = 2.77$ inches
$R_b = 2.87$ inches
$R_c = 15.50$ inches
$\theta = 26°$ Referring now to the sectional view shown in FIG. 5, a tensioning rod 62 having internal threads therein is mounted inside hollow post member 20. A screw 64 is threadedly coupled to tension rod 62 through the upper surface of base member 16. A washer 66 is interposed between the screw head 68 and the surface of base 16. A female knob 28 is threadedly affixed to the other end of tension rod 62. The slide assembly 24 is formed around post member 20 and is movable in a vertical direction. FIG. 4 shows the vertical pressure release member 30 in a position wherein the slide assembly 24 is maintained in a selected position. Depression of the lever will allow the slide assembly 24 to move freely in the vertical direction to the selected position at which point the lever is released, locking the assembly to the selected position. A paddle clamp mounting 70 is provided adjacent one side of the slide assembly 24, paddle support arm 34 being inserted in the aperture formed therein. The paddle support arm 34 is separated from the slider assembly 24 by washer 72. The lever assembly 34 includes an internal threaded post 74 which extends through an aperture in paddle clamp mounting 70 and extends through an aperture in the slide assembly 24. A washer 26 is interposed between the lever head and one surface of paddle clamp mounting 70. Internal threaded post, or screw set, 78 is affixed at one end to knob 32, the other end engaging the surface of slide assembly 24 as shown.

The manner of adjusting the independent compression device 10, and the compression paddle 14, in particular, has been set forth hereinabove with reference to FIG. 3.

The independent compression device set forth hereinabove is independent of the x-ray system being utilized, is lightweight and portable and includes a compression paddle made of transparent plastic which allows the user to visualize breast position and eliminate skin folds prior to x-ray exposure, reducing the number of reimages which normally may be necessary. The compression paddle is adjustable in a number of directions providing positioning flexibility which allows improved images to be produced because of the control on paddle position. The unique curved design of the lower surface of the compression paddle in addition gently holds the opposite breast out of the image area, the paddle being comfortable and smooth against the breast to be imaged.

While the invention has been described with reference to its preferred embodiment, it will be understood by those skilled in the art that various changes may be made and equivalents may be substituted for elements thereof without departing from the true spirit and scope of the invention. In addition, many modifications may be made to adapt a particular situation or material to the teaching of the invention without departing from its essential teachings.

What is claimed is:

1. Apparatus for compressing and positioning an object to be examined by subjecting the object to penetrating radiation comprising:
    a base member,
    a member supported by said base member and extending along a first vertical axis,
    a slide assembly mounted to said vertically extending member and adapted for movement therealong,
    a compression member extending along a first horizontal axis and mounted to said slide assembly via a support member,
    means operatively associated with said slide assembly for enabling said compression member to be positioned in the direction of said first horizontal axis,
    means operatively associated with said slide assembly for enabling said support arm to be pivoted about said first horizontal axis, and
    means operatively associated with said slide assembly for enabling said compression member to be vertically tilted relative to said first vertical axis.

2. The apparatus as defined in claim 1 further including means operatively associated with said slide assembly for enabling said slide assembly to be moved to predetermined positions along said vertically extending member.

3. The apparatus as defined in claim 2 further including means for enabling said vertically extending member to be rotated about said first vertical axis.

4. The apparatus as defined in claim 3 wherein said compression member comprises a rear portion to which said support member is affixed, first and second sidewalls and a curved bottom portion, the curved bottom portion compressing the object being examined.

5. The apparatus as defined in claim 4 wherein said curved bottom portion terminates in an upwardly extending front portion, said front portion being inclined at an angle relative to a second vertical axis.

6. Apparatus for compressing and positioning an object to be examined by subjecting the object to penetrating radiation generated by a source thereof, said compressing apparatus being independent of said source of penetrating radiation comprising:
    a base member,
    a member supported by said base member and extending along a first vertical axis,
    a slide assembly mounted to said vertically extending member and adapted for movement therealong,
    a compression member extending along a first horizontal axis and mounted to said slide assembly via a support member, means operatively associated with said slide assembly for enabling said compression member to be positioned in the direction of said first horizontal axis,
    means operatively associated with said slide assembly for enabling said support arm to be pivoted about said first horizontal axis, and
    means operatively associated with said slide assembly for enabling said compression member to be vertically tilted relative to said first vertical axis.

7. The apparatus as defined in claim 6 further including means operatively associated with said slide assembly for enabling said slide assembly to be moved to predetermined positions along said vertically extending member.

8. The apparatus as defined in claim 7 further including means for enabling said vertically extending member to be rotated about said first vertical axis.

9. The apparatus as defined in claim 8 wherein said compression member comprises a rear portion to which said support member is affixed, first and second sidewalls and a curved bottom portion, the curved bottom portion compressing the object being examined.

10. The apparatus as defined in claim 9 wherein said curved bottom portion terminates in an upwardly extending front portion, said front portion being inclined at an angle relative to a second vertical axis.

11. The apparatus as defined in claim 10 wherein said source of penetrating radiation is an x-ray device, the penetrating radiation comprising x-rays.

12. The apparatus as defined in claim 10 further including an imaging member responsive to said penetrating radiation, the object to be examined being compressed against said imaging member by said compression member whereby an image of the internal structure of said object is formed on said imaging member by the penetrating radiation passing through said object.

13. An apparatus for compressing and positioning an object to be examined by subjecting the object to penetrating radiation, the radiation passing through the object forming an image of the internal structure thereof on an imaging member responsive to said penetrating radiation, the improvement comprising:
    a compression paddle comprising a rear portion to which is affixed a support member, first and second sidewalls and a curved bottom portion, the curved bottom portion compressing the object being examined.

14. The improvement as defined in claim 13 wherein said curved bottom portion terminates in an upwardly extending front portion.

15. The improvement as defined in claim 14 wherein said upwardly extending front portion is inclined at an angle relative to the vertical.

* * * * *